United States Patent
Bhikhabhai (12)

(10) Patent No.: US 6,410,274 B1
(45) Date of Patent: Jun. 25, 2002

(54) PLASMID DNA PURIFICATION USING DIVALENT ALKALINE EARTH METAL IONS AND TWO ANION EXCHANGERS

(75) Inventor: Ramagauri Bhikhabhai, Uppsala (SE)

(73) Assignee: Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/319,212

(22) PCT Filed: Sep. 28, 1998

(86) PCT No.: PCT/SE98/01672

§ 371 (c)(1),
(2), (4) Date: Oct. 7, 1999

(87) PCT Pub. No.: WO99/16869

PCT Pub. Date: Apr. 8, 1999

(30) Foreign Application Priority Data

Sep. 30, 1997 (SE) ............................................. 9703532

(51) Int. Cl.⁷ ......................... C12P 19/34; C12N 11/00; C07H 21/00
(52) U.S. Cl. ....................... 435/91.1; 435/174; 536/22.1
(58) Field of Search ........................ 435/89, 91.1, 174; 536/22.1, 23.1

(56) References Cited

U.S. PATENT DOCUMENTS 5,561,064 A   10/1996   Marquet et al. ......... 435/320.1

FOREIGN PATENT DOCUMENTS

WO   9636706   11/1996

OTHER PUBLICATIONS

Raymond, et al., Analytical Biochemistry, vol. 173, pp. 125–133 (1988).*

* cited by examiner

Primary Examiner—David M. Naff
(74) Attorney, Agent, or Firm—Birch, Stewart, Kolasch & Birch, LLP

(57) ABSTRACT

A process is provided for large scale purification of plasmid DNA to obtain plasmid DNA of pharmaceutical grade. Steps of the process include lysing cells such as by alkaline lysis to obtain a lysate containing plasmid DNA, chromosomal DNA and RNA, precipitating most of the RNA and Chromosomal DNA by adding divalent alkaline earth metal ions such as provided by calcium chloride, removing the precipitated RNA and chromosomal DNA, and contacting the lysate with an anion exchange matrix to obtain purified plasmid DNA. The anion exchange matrix may be cross-linked agarose containing anion exchange groups bound to the matrix via an extender such as dextran. The anion exchange groups may be quaternary ammonium groups. The purified plasmid DNA may be further contacted with an anion exchange matrix such as hydrophilyzed polystyrene/divinyl benzene substituted with quaternary ammonium groups to obtain purified plasmid DNA of gene therapy grade.

10 Claims, 4 Drawing Sheets

PLASMID DNA PURIFICATION USING DIVALENT ALKALINE EARTH METAL IONS AND TWO ANION EXCHANGERS

This application is the national phase under 35 U.S.C. §371 of PCT International Application No. PCT/SE98/01672 which has an International filing date of Sep. 28, 1998 which designated the United States of America.

FIELD OF THE INVENTION

The present invention relates to a process for purification of plasmid DNA. The process is particularly concerned with an improved method of separation of plasmid DNA on an anion exchange matrix.

BACKGROUND OF THE INVENTION

The development of gene therapy has increased the demand for highly purified gene vectors such as plasmid DNA. The problem with the purification of plasmid DNA is to completely remove other cell components such as host proteins, endotoxins, chromosomal DNA and RNA. For molecular biology purposes plasmid DNA is purified in laboratory scale in several steps including centrifugation, extraction with toxic solvents, enzyme treatment and chromatographic separation.

A common purification protocol can be described as follows: After harvesting and lysis of the cells, the crude lysate is centrifuged to separate cell debris. The lysate is further treated with organic solvents, such as phenol/chloroform to extract proteins. The content of RNA is reduced by treatment with enzymes like RNase. Finally the plasmid DNA is purified by centrifuging the lysate to equilibrium in cesium chloride-ethidium bromide density gradients. Alternatively or in addition chromatography purification can be used. There are variations of these type of steps in other protocols. However, these type of purification methods are not suitable for large scale production of pharmaceutical grade plasmid.

The disadvantages with known purification methods are several. The density gradient step is cumbersome and not suited for large scale production. There is also an introduction of carcinogenic and expensive chemicals which are hazardous to work with and which have to be eliminated from the final product. When RNase is added to hydrolyze RNA or degrade RNA into ribonucleotide subunits there is always a risk of adding unwanted proteins including DNase from other animals. For the production of pharmaceutical grade DNA unwanted proteins should be avoided.

Different chromatographic methods have been used for plasmid DNA purification, such as size exclusion chromatography, or gel filtration, hydroxyapatite, ion exchange and reversed phase chromatography. Size exclusion chromatography or gel filtration is not practical as a first chromatography step as very large columns are needed. Hydroxyapatite chromatography has other disadvantages. The matrix is difficult to regenerate and does not have a high capacity for plasmids. Besides, diafiltration has to be used to change the buffer system. With reversed phase chromatography the use of organic solvents makes the method difficult to use in large scale.

Ion exchange chromatography is the most commonly used chromatography method. Plasmid DNA, chromosomal DNA and RNA all bind to anion exchangers as they have similar charge properties. Most of the commercial kits available use RNase to hydrolyse RNA in the clear lysate before applying the sample to the column. In most of the purification protocols used, the sample has either been treated with RNase or heated or isopropanol precipitated or phenol extracted. WO 96/36706 and WO 95/21178 are examples of these methods. For large scale production precipitation and extraction are difficult to carry out. The RNase used has to be of high grade purity produced from reliable sources.

If the lysate prepared by alkaline lysis method is applied directly to the ion exchanger without further treatment, plasmid, chromosomal DNA and most of the contaminating material including RNA and pigment bind to the column matrix. As the content of RNA of the lysate is about 80% and chromosomal DNA is about 2–20% (depending on the lysing method) and plasmid DNA is only 1–2%, the capacity of the column for binding plasmid DNA is greatly reduced due to the fact that the binding sites are occupied by RNA and chromosomal DNA. Thus, the amount of contaminating material has to be reduced in the lysate in some manner before the lysate is added to the chromatography matrix.

SUMMARY OF THE INVENTION

The object of the present invention is to provide an improved process for large scale purification of plasmid DNA to obtain plasmid DNA of pharmaceutical grade.

A further object of the invention is to present a purification method which is simple and effective without the draw-backs of known methods as mentioned above.

The objects of the invention are achieved by the process for purification as claimed in the claims. According to the invention a process for purification of plasmid DNA by separation on an insoluble matrix is obtained. The process comprising:

a) lysing cells containing said plasmid DNA to obtain a lysate;

b) adding divalent alkaline earth metal ions to the lysate from a);

c) removing precipitated compounds from the lysate from step b);

d) contacting the lysate from step c) with an anion exchange matrix to obtain purified plasmid DNA.

DETAILED DESCRIPTION OF THE INVENTION

Figure 1A:
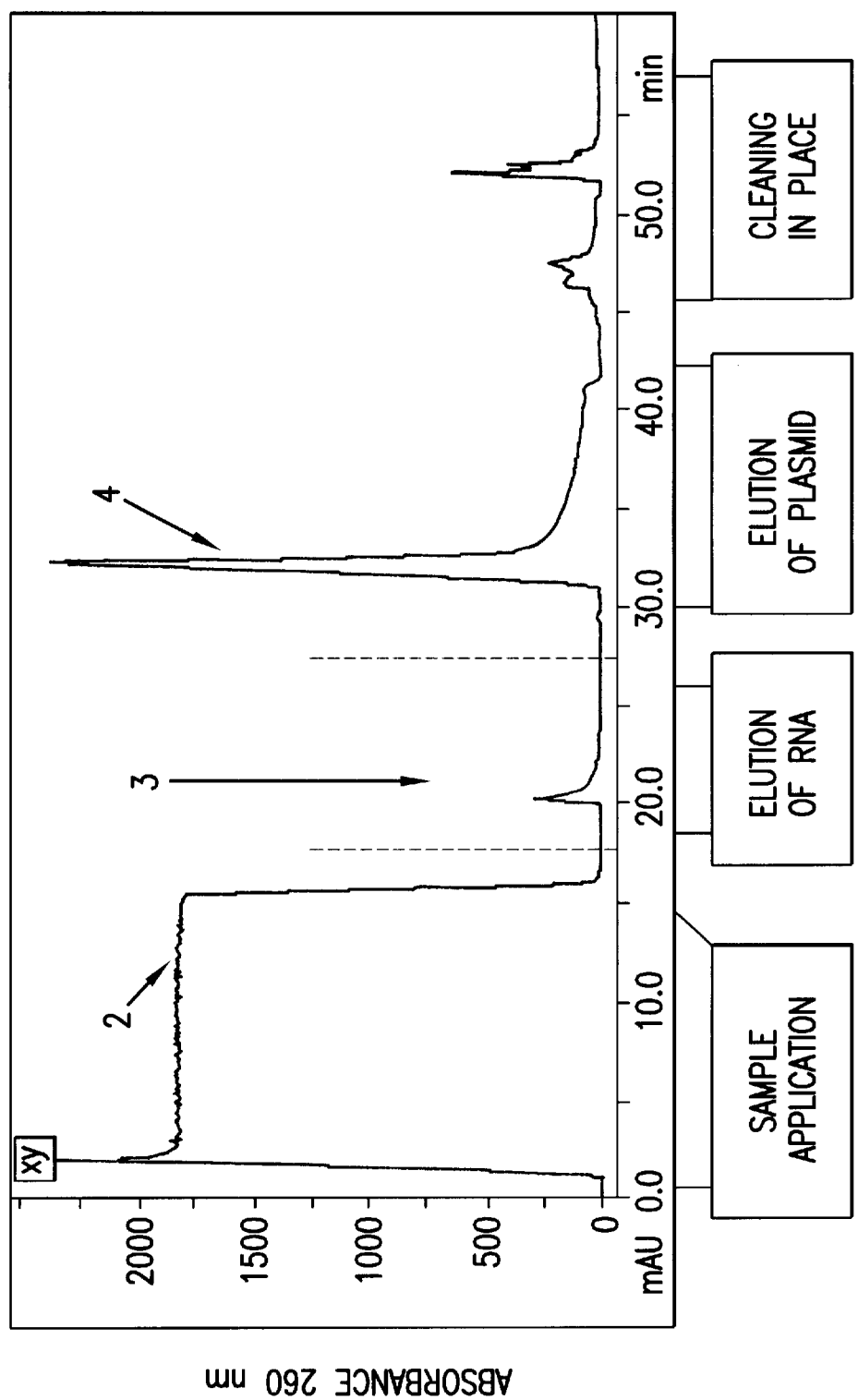
FIGS. 1A and 1B. Eluants of lysate on a 1 ml Q Sepharose XL column.

With the present invention it was found that the addition of divalent alkaline earth metal ions to the lysate was a simple and effective method to remove most of the impurities such as contaminating RNA and chromosomal DNA before adding the lysate to the chromatography matrix. The addition of the metal ions has a multiple effect on the nucleic acids. First, most of the RNA is precipitated. Also most of the chromosomal DNA and part of the open circular plasmid is removed. Further, the addition of the metal ions creates a difference in charge between RNA and plasmid DNA which facilitate the separation on the chromatography matrix of the RNA remaining in the lysate after precipitation. The alkaline earth metal ions are added in the form of a salt or salt solution. In a preferred embodiment $CaCl_2$ is added as alkaline earth metal salt.

CaCl₂ has been suggested earlier for plasmid DNA purification. According to G. J. Raymond, P. K. Bryant III, A Nelson, and J. D. Johnson (1988) *Analytical Biochemistry* 173, 125–133, CaCl₂ has been used to precipitate RNA, but the use of CaCl₂ is combined with phenol extraction and ethanol precipitation before adding the lysate to gel filtration. Thus, this purification protocol is more cumbersome and has the draw backs with toxic solvents and with the large columns of gel filtration. The inventors of this protocol did not realise that CaCl₂, could be used in a more efficient way.

The process according to the invention is performed in two steps, the sample preparation and the chromatographic procedure. The expression "chromatographic procedure" is meant to include also batchwise procedure. In the first step the plasmid is extracted from the cells and the sample is prepared for the chromatographic purification. The cells are lysed, preferably by alkaline lysis using standard protocols (Maniatis, T, Fritsch, E. F. and Sambrook, J. (1982) Molecular Cloning: A Laboratory Manual, Cold Spring Harbour Laboratory Press, Cold Spring Harbour, N.Y.). Then the lysate is treated with the metal ions to precipitate soluble RNA and chromosomal DNA. After removal of the precipitate the clear lysate is subjected to anion exchange chromatography. In a preferred embodiment two anion exchangers are used. In the first anion exchanger the operating conditions are optimised in order to selectively bind the plasmid to the matrix, whereas most of the RNA passes through the matrix unbound. The second anion exchanger are used to further remove traces of RNA and chromosomal DNA and to obtain plasmid of gene therapy grade. The final plasmid product is highly pure without RNA and chromosomal DNA and structurally the plasmid is to 93–100% in supercoiled form. With the process according to the invention several advantages are obtained such as speed and scaleability of the process, high purity of the product, no addition of foreign proteins, operational simplicity and direct application of sample without any diafiltration.

The plasmid used in the present invention can be of any origin. Most commonly, micro organisms like *E.coli* are used for culturing the plasmids, out the use of host cells is not limited and can be prokaryotic or eukaryotic cells. The host cells harbouring the plasmid can be cultivated in a number of ways, well known in the art, e.g. in incubator, bioreactor, fermentor etc. The plasmid can be of any size. It can be a high copy number or low copy number per cell. The plasmid can carry any gene (either genomic or synthetic), encoding protein or peptide of interest from any source. The culturing of the host cells as well as the exploitation of the plasmid for gene therapy, is well known in the state of the art.

After culturing the host cells containing the plasmid, the cells are recovered by centrifugation or filtration. The cell can be stored in a freezer or processed immediately.

Then the cells are lysed according to standard methods. There are a number of methods known to lyse the cells. Most commonly used are alkaline lysis (as mentioned above) or alkaline extraction (Birnboim, H. C. and Doly, J. (1979) Nucleic Acids Res 7 1513). The alkaline lysis used in the present invention is carried out in three steps:

1. Resuspension of Cells in Buffer.

The cells are suspended in a suspension buffer. The composition of this buffer is not limited and includes reagents recognized as safe (GRAS) by regulatory authorities. The most commonly used buffer is Tris-Cl, pH 8.0, 25 EM glucose and 10 mM EDTA. The choice of ion strength and pH of the buffer is well within the skill of the ordinary artisan.

2. Lysis of the Cells.

An alkaline solution together with an ionic detergent is added. The most commonly used buffer is 0.2 M NaOH and 1% SDS (sodium dodecyl sulfate). At pH 10–12.5 linear DNA molecules are denatured whereas there is no effect on supercoiled plasmid.

3. Neutralisation.

Neutralisation at a high salt concentration is performed to precipitate chromosomal DNA, cellular RNA and proteins in complex with SDS. A buffer of high salt concentration can be used, such as e.g. 3M potassium acetate.

After lysing the cells, cell debris and other precipitated impurities are removed. The precipitated chromosomal DNA and proteins are separated by a combination of techniques such as centrifugation and filtration through different sizes of filtering devices available in the market.

Then, according to the invention, alkaline earth metal ions are added to the obtained clear lysate. The ions are added in the form of salt or salt solution. Preferably CaCl₂ is added. By the addition of the metal ions, RNA and chromosomal DNA are precipitated. In this step, the amount of RNA and chromosomal DNA, being the major impurities of the lysate, is reduced. Alternatively, the addition of the alkaline earth metal ions can be made just after the neutralisation, before removal of cell debris.

The amount of alkaline earth metal ions added to the lysate should be enough to precipitate the impurities of the lysate. However, if the amount is too high there is a risk that also the plasmid will precipitate The suitable amount alkaline earth metal ions can be determined by the skilled man. As general outlines it was found that when CaCl₂ is used, a suitable concentration of the salt in the lysate is within 0.1–0.4 M. Preferably the concentration of CaCl₂ is 0.2 M.

After reaction of CaCl₂ the precipitate is removed, suitably by filtration or centrifugation, in the same manner as mentioned above.

The obtained cleared lysate may then be added to an anion exchange matrix without further treatment. In the present invention it was surprisingly found that, not only most of the RNA, the chromosomal DNA and part of the open circular plasmid were removed by the CaCl₂ precipitation, but the CaCl₂ addition also creates a difference in charge between the remaining RNA (about 2%) and plasmid DNA. This charge difference leads to the possibility to use an ion exchanger to which plasmid and chromosomal DNA band to the matrix but most of the RNA passes through the column. By. then choosing the appropriate solvent the plasmid is eluted while the chromosomal DNA is still bound to the matrix. The chromosomal DNA is removed during regeneration of the column.

The anion exchange matrices used in the present invention can be any matrix available in the market. There are many commercial products available based on different resins or polymer, e.g. agarose or cross-linked agarose (such as Sepharose®, Pharmacia Biotech), dextran, polystyrene/divinylbenzene (MonoBeads®, SOURCE®, Pharmacia Biotech), coated polystyrene, acrylic polymer, vinylic grafted polymer, or vinylic polymer, different silica based resins such as silica-dextran, silica-acrylic polymer and silicapolyethyleneimine.

The anion group attached to the matrix can vary from quaternary amino groups (Q), quaternary aminomethyl-(QMA), quaternary aminoethyl-(QAE), triethyl aminomethyl-(TEAE), triethyl aminopropyl-(TEAP), polyethyleneimine-(PEI), diethyl aminoethyl-(DEAE), polyaminoethyl groups (PAE) and others.

In a preferred embodiment of the present invention the anion exchange groups are bound to the base matrix via extenders such as described in SE 9700383-4 (filed Apr. 2, 1997), the content of which is hereby enclosed by reference. It was found in the present invention that the chromatography purification of the plasmid was very efficient with this type of matrix. The positive effect caused by the extender is believed to depend on the fact that the extender will provide the inner surfaces (pore surfaces) and/or outer surfaces of the matrix beads with a flexible polymer layer which is permeable to macromolecules and other molecules are allowed to pass the bed. This will cause an increase in the effective interaction volume as well as in the steric availability of the anion exchange groups. This in turn will increase the mass transfer rate as well as the total capacity.

Suitable extenders should be hydrophilic and contain a plurality of groups selected from e.g. hydroxy, carboxy, amino, repetitive ethylene oxide ($-CH_2CH_2O-$), amido etc. The extender may be in the form of a polymer. Hydrophilic polymeric extenders may be of synthetic origin or of biological origin. Typical synthetic polymers are polyvinyl alcohols, polyacryl- and polymethacrylamides, polyvinyl ethers etc. Typical biopolyners are polysaccharides, such as starch, cellulose, dextran, agarose. The preferred polymeric extenders are often water-soluble in their free state, i.e. when they are not attached to the base matrix.

The length (size) of the optimal extender will depend on several factors, such as number of attachment points to the base matrix of the beads, type of extender, type and size of anion groups etc. For polymeric extenders for which attachment and/or cross-linking is possible at several monomeric units, it is believed that larger extenders are preferred. It is believed that the most suitable polymers should contain at least 30 monomeric units, which for polysaccharides like dextran indicates a $M_w>5000$ Da.

The base matrix of the beads may be of organic or inorganic nature. It may be porous or non-porous. Usually it is a polymer, such as glass, a synthetic polymer or a biopolymer. The base matrix may be a hydrophilic polymer such as styrene-divinyl benzene copolymer, which has been hydrophilized on inner and/or outer surface by being coated with the appropriate hydrophilic polymer or by other means. Alternatively, the base matrix may be a water-insoluble hydrophilic polymer, e.g. agarose, cellulose, dextran, starch, etc. which has been cross-linked to give the desired porosity and stability, if necessary. A preferred base matrix in the present invention is based on cross-linked agarose with dextran as extenders.

The chromatographic purification of the cleared lysate is mainly carried out according to principles known in the art. Suitable running conditions, such as the ionic strength of the buffer at which the plasmid will bind and elute from the matrix, can be optimised by the skilled man. However there are some details in the process which have been found to result in a very efficient purification. The chromatographic process can be described accordingly:

A chromatographic column is packed with the desired anion exchanger matrix and equilibrated with an acidic buffer. The pH of the equilibration buffer should be the same as that of the clarified lysate. The flow rate used is as recommended by the manufacturer. The clarified lysate is passed through the column and the column is washed with the acidic buffer. In this process more than 80% of RNA passes through the column. The plasmid, chromosomal DNA and remaining RNA bind to the column. The flow rate used is the same as during equilibration. The use of an acidic buffer is not the most common in anion exchange chromatography where a pH of 8.0 is a normal value for the equilibrium buffer. It was found in the present invention that by using an acidic pH the charge difference between RNA and plasmid is greater. Then RNA is passed through the column more effectively. Besides, the process is more simple in this manner as the pH of the lysate obtained in the first step is acidic. The acidic pH used is suitably below 6 but above 4, preferably about 5.5. This is a preferred embodiment of the invention.

The operation of the process is then optimised in a manner that the bound or adsorbed RNA and the plasmid are recovered in separate fractions. The elution buffer used is more alkaline (between pH 7–8). The salt concentration or ionic strength of the buffer in this step is chosen so that RNA but not plasmid DNA is eluted during this step. When this step is performed in the usual way, some RNA still remains bound to the matrix, which necessitates washing the column with large volumes of buffer. In the present process it was found that if the ionic strength of the buffer is reduced, RNA elutes more effectively. Thus, the elution of RNA starts with one ionic strength of the buffer and proceeds with a buffer of a lower ionic strength. In this manner nearly all RNA is detached from the matrix The respective values of the buffers can easily be determined by the skilled man by running a normal salt gradient and checking at which conductivity value the plasmid elutes. An ionic strength well below this value should then be chosen. This manner of elution is also a preferred embodiment of the invention.

To elute the plasmid the pH and the ionic strength of the buffer is increased. A suitable pH is about 10. The buffer is added to the column and in order to release all plasmid the column is incubated in the buffer for a few minutes. Then the plasmid is eluted with a very slow speed, only one fifth of the recommended speed. This method increases the yield with about 20%.

In a following cleaning step chromosomal DNA is removed and at the same time the column is cleaned to be used for the next run.

In a preferred embodiment of the invention a second anion exchange chromatography step is used. The intention with a second anion exchanger is to remove slight impurities of RNA and chromosomal DNA from the plasmid fractions. The chromosomal DNA vary in size and charge, and hence they bind to the matrix with different ionic strengths. By using a flat gradient of salt (e.g. sodium chloride) over the column to elute the plasmid, most of the chromosomal DNA will be removed in the fractions before and after the plasmid fractions.

The second chromatography purification is run according to normal conditions well known in the art. The column is equilibrated with the equilibrium buffer having a pH>6 and the ionic strength of the buffer should not exceed the ionic strength at which the plasmids bind the matrix. The plasmid fractions are diluted in a manner that the resulting ionic strength of the sample solution allows the plasmid to bind to the matrix. The plasmid is then eluted by passing a linear gradient of buffer, with increasing ionic strength over the column. During this process, the plasmid highly purified (gene therapy grade or pharmaceutical—grade) and at the same time most of the chromosomal DNA is removed. It is well within the skill of the artisan in this technical field to determine the ionic strength of the buffers in these steps. The buffers used in both the chromatography steps are buffers normally used in anion exchange chromatography. The most commonly used buffer substances are Tris or phosphate. During the elution of the bound nucleic acids from the column,the ionic strength of the buffer is increased by adding salts such as sodium chloride to the buffer solution.

The anion exchange matrices used in this second chromatographic purification can be chosen among known anion exchangers as mentioned above. The matrix can be of the same type as in the first ion exchange step or it can be of a different type. In a preferred embodiment the matrix in the second ion exchange step is a hydrophilized polystyrene/divinyl benzene matrix substituted with quaternary ammonium groups.

The invention will now be illustrated by the following non-limiting examples. With parts and percent are meant parts by weight and percent by weight if not stated otherwise.

In the examples a plasmid with low copy number has been chosen. It is well known to those skilled in the art that the yield of the plasmid from the chromatographic purification would be much higher in the case of plasmids with high copy number. In the first chromatography step the anion matrix is a cross-linked agarose matrix with dextran as extenders. The anionic groups are Q groups. (Q Sepharose® XL from Pharmacia Biotech). In the second chromatography step a rigid polystyrene/divinyl benzene matrix with Q groups are used. (SOURCE® 15Q from Pharmacia Biotech).

EXAMPLE 1

Cell Lysis 1. 31 g of bacterial cell paste (*E.coli*) are suspended in 341 ml of suspension buffer (25 mM Tris-Cl, 25 mM Glucose, 10 mM EDTA, pH 8.0)

2. 310 ml of 0.2 M NaOH, 1% SDS are added to lyse the cells and the solution is let to stand for 15 minutes. The solution is shaken very gently once or twice. The solution becomes viscous.

3. 155 ml of neutralisation buffer (3M KOAc pH 5.5) are added. A white precipitate is formed.

4. The sample is centrifuged at 14 000×g for 30 min.

5. The solution is carefully filtered over a loosely packed glass wool.

6. 2M $CaCl_2$ solution is added to obtain a final concentration in the solution of 0.2 M $CaCl_2$. The solution is left to stand for at least 15 minutes at room temperature.

7. The fine precipitate is centrifuged and the solution filtered.

8. The clarified lysate should be clear enough to be applied on the column. Filtration can be done again if the solution is not clear.

9. The conductivity of the sample is checked and adjusted to 60 mS/cm by diluting with water. The lysate is ready to be applied to the column packed with Q Sepharos XL.

EXAMPLE 2

First Anion Exchange Chromatography Step

Gel matrix: Q Sepharose XL

Column size: 10 ml, 1.6 cm i.d.×5.0 cm

Chromatography System: ÄKTA explorer® from Pharmacia Biotech.

Equilibration Acidic Buffer: 0.5 M KOAc, pH 5.5

Elution Buffer 1 for RNA: 25 mM Tris-Cl, 1 mM EDTA, 0.75 M NaCl, pH 8.0

Elution Buffer 2 for RNA: 25 mM Tris-Cl, 1 mM EDTA, 0.5 M NaCl, pH 8.0

Buffer with high salt concentration: 25 mM Tris-Cl, 1 mM EDTA, 1.2 M NaCl, pH 8.0

Elution buffer for plasmid: 50 mM Sodium Phosphate, 1 M NaCl, pH 9.6

Buffer for cleaning in place: 2 M NaCl, 0.5 M NaOH

Flow velocity; 300–600 cm/hr

Column volume=CV

1. The column is equilibrated with acidic equilibration buffer

2. The sample is applied.

3. The column is washed with 5 CV of equilibration acidic buffer.

4. Further washing with 3 CV of elution buffer 1 for RNA.

5. Further washing with 5 CV of elution buffer 2 for RNA. Notice that salt concentration in buffer 2 is lower than that in elution buffer 1 of RNA.

6. 1.1 CV of elution buffer of plasmid is passed over the column.

The pumps are stopped, flow rate=0 ml/min for five minutes.

The plasmid is eluted with 3.5 CV of elution buffer for plasmid at a flow rate of 60 cm/hr.

Regeneration

1. The column is washed with 5 CV of cleaning in place buffer.

2. The column is equilibrated with the equilibration acidic buffer for the next run.

EXAMPLE 3

Second Anion Exchange Chromatography Step

Gel matrix: SOURCE 15Q

Column size: 6 ml, 16 mm i.d.×30 mm (RESOURCE Q® from Pharmacia Biotech)

Chromatography System: ÄKTA explorer

Equilibration Buffer A: 25 EM Tris-Cl, 1 mM EDTA, pH

Buffer 3 with high salt; 25 mM Tris-Cl, 1 mM EDTA, 1.0 M NaCl, pH 8.0

Buffer for cleaning in place: 2 M NaCl, 0.5 M NaOH

Gradient: 40–100% B, 20 CV

Flow velocity: 150–900 cm/hr

The pooled fractions from the first chromatography step are diluted and the conductivity is adjusted to 38 mS/cm. 140 ml of the sample are applied to the column pre equilibrated with buffer A. The plasmid is eluted using a linear gradient of 40–100% buffer B. The fractions were collected.

EXAMPLE 4

Scaling Up to 100 ml Column in the First Chromatography Step

The process is scaled up to 100 ml column filled with Q Sepharose XL.

Purity Check and Analysis of the Pooled Fractions From a Plasmid Peak

Each fraction is analysed on agarose gel electrophoresis to check the content of the sample. RNA, plasmid (supercoiled and open circular) and chromosomal DNA can be easily identified.

Each fraction is analysed by reversed phase chromatography to quantify the amount of plasmid and RNA in the sample.

Each fraction is analysed on analytical anion exchange chromatography to quantify supercoiled and open circular plasmid.

Each fraction is also analysed for quantification of chromosomal DNA.

Each fraction was assayed for endotoxin and protein concentration. The details of the analysis methods are also found in P. Wils, et. al., 1997, Gene Therapy, 4, 323–330.

Results:

FIG. 1A: Chromatogram for anion exchange chromatography (optimization of the first chromatography step of the process on 1 ml column). 2, 3 and 4 refer to the fractions which were analysed by agarose electrophoresis in FIG. 1B.

System: ÄKTAexplorer
Detection: 260 nm
Column size: 1 ml

Figure 1B:
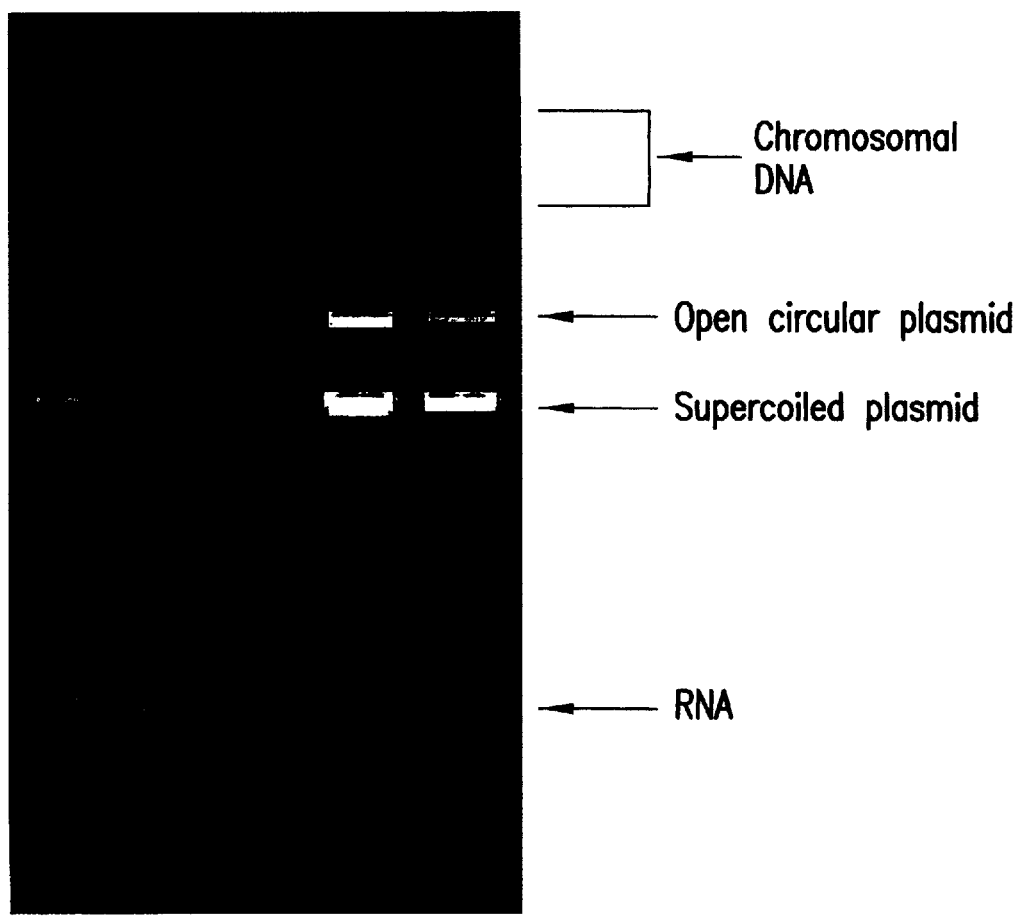

FIG. 1B: Analysis by agarose gel electrophoresis. Lane 1 is clear lysate, the sample applied to the column. Lane 2, 3, 4 and 5 are fractions from FIG. 1 marked with the same numbers as the lane.

Lane 1: Clear lysate
Lane 2: Flow through, fraction containing RNA
Lane 3: RNA fraction
Lane 4: Plasmid fraction
Lane 5: Plasmid, fraction diluted ×2

Figure 2:
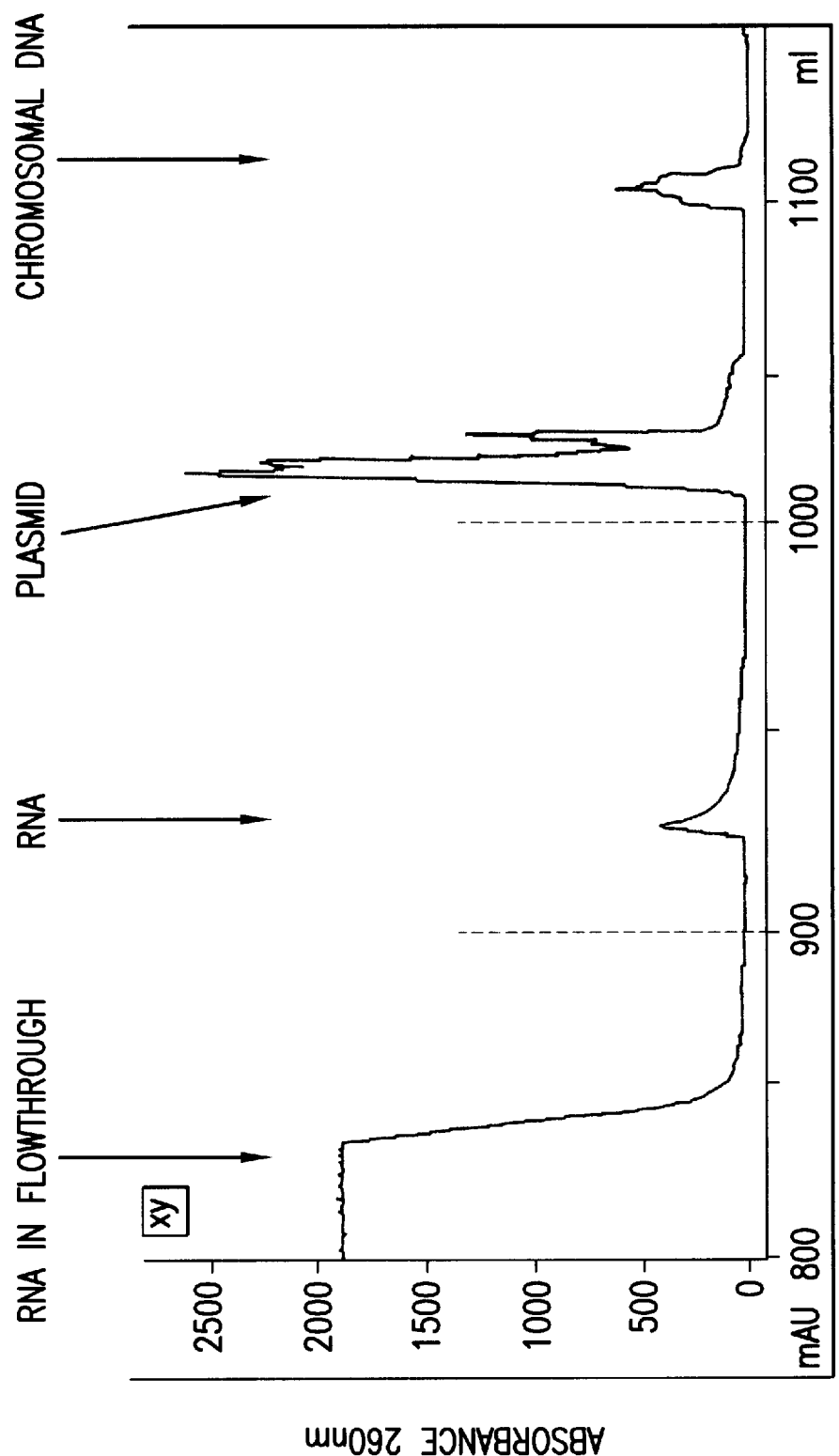
FIG. 2. Eluants of lysate on a 10 ml Q Sepharose XL column.

FIG. 2: First chromatography step. Purification of plasmid from 31 g cells on Q Sepharose XL.
Detection: 260 nm, Column size: 10 ml, 16 mm i.d.×50 mm FIG. 3: Second chromatography step. Futher purification of plasmid fractions from FIG. 2 on RESOURCE Q (prepacked column of SOURCE)
Detection. 260 nm, Column size: 6 ml, 16 mm i.d × 30 mm Table 1. The analysis of plasmid fraction from the chromatographic purification using 10 ml of Q Sepharose XL (FIG. 2), RESOURCE Q (FIG. 3) and 100 ml of Q Sepharose XL.

|  | Step 1 Q Sepharose XL | Step 2 Resource Q | Step 1 Q Sepharose XL |
| --- | --- | --- | --- |
| Column size | 10 ml | 6 ml | 100 ml |
| Amount of plasmid applied in mg | 6.2 | 4.6 | 56 |
| Analysis of plasmid peak |  |  |  |
| [1]Total NA in plasmid peak (mg) | 5.4 | 3.8 | 43 |
| [2]Plasmid concentration by RPC (mg) | 4.8 | 3.9 | 38 |
| RNA concentration by RPC % | 4 | 0 | 4.6 |
| [3]Chromosomal DNA % | 2 | 0.6 | 1.3 |
| [4]Supercoiled plasmid % | 93 | 100 | 63 |
| Open circular plasmid % | 7 | 0 | 27 |
| [5]Endotoxin EU/mg | n.d. | n.d. | 1.5 |
| [5]Protein % | n.d | n.d. | 2.2 |
| Purity of plasmid in plasmid peak in % | 90 | 99.4 | 90 |
| Plasmid yield % | 78 | 66 | 67 |

Figure 3:
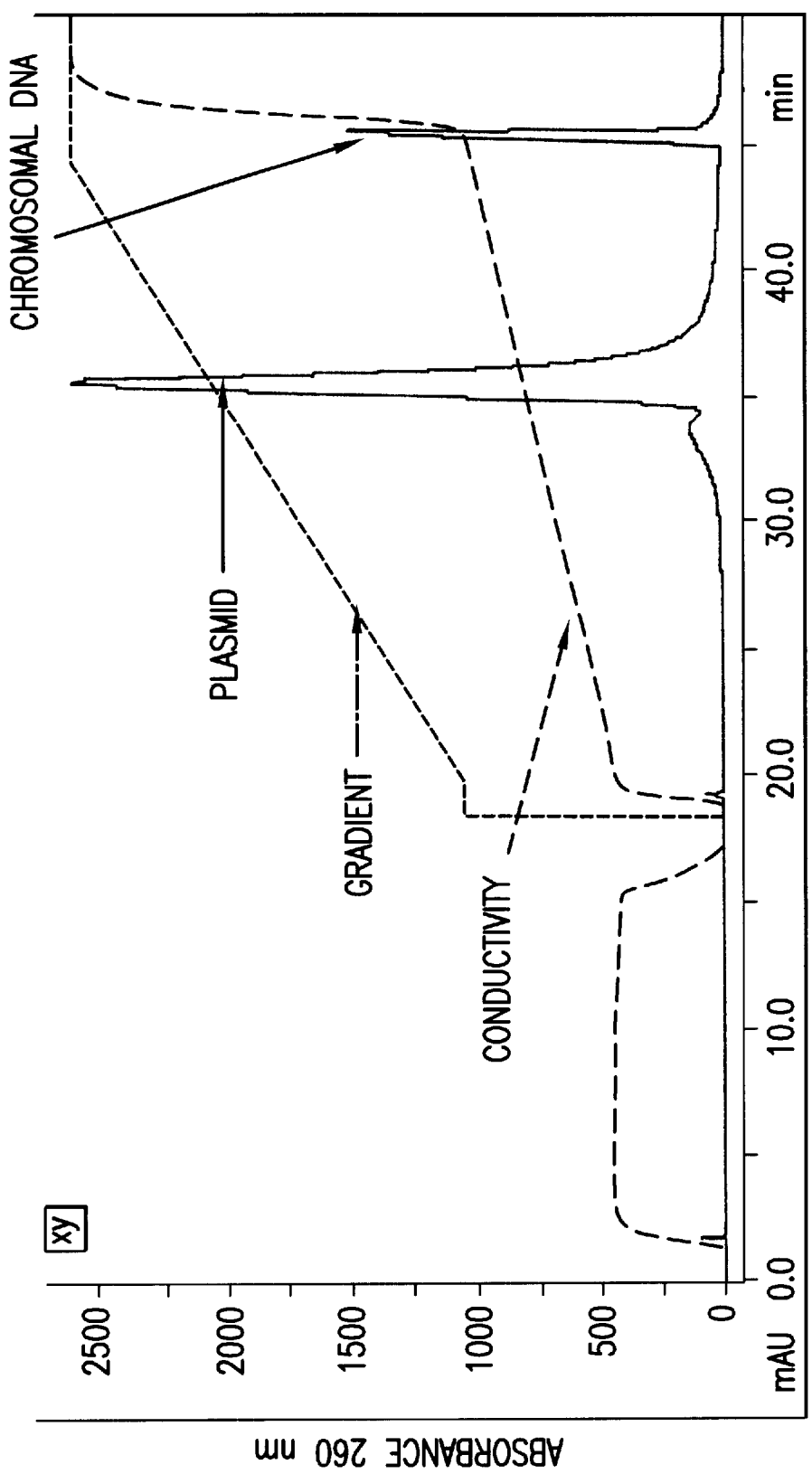
FIG. 3. Further purification of plasmid fraction on a RESOURCE 15Q column.

[1]NA = Nucleic acid. 50 μg/ml of nucleic acid has an absorbance of one unit at 260 nm.
[2]Analysis of plasmid was determined by reversed phase chromatography (RPC).
[3]Chromosomal DNA was quantified after PCR amplification using primers in the E. coli galK gene.
[4]The amount of supercoiled and open circular plasmid was analysed by anion exchange chromatography.
[5]Endotoxins were performed using LAL kit and protein concentration was measured using the Pierce Micro BCA assay.
n.d. = not determined During sample preparation it was observed that there is a two fold decrease in RNA and chromosomal DNA when calcium chloride is added to the lysate. The clear lysate (as described in example 1) was used for chromatography on Q Sepharose XL. First the process was optimized on a 1 ml column (FIGS. 1A and 1B) and then scaled up to 10 ml column (FIG. 2) as described in example 2. The fractios containing plasmid were pooled and further purified on RESOURCE 15Q column (FIG. 3).

The fractions were analysed for plasmid DNA and the contaminants RNA, chromosomal DNA, endotoxins and proteins were measured in the first chromatography step (Table 1) The percentage of supercoiled and open circular plasmid was determined in the final purified plasmid fraction. The results show that nearly all RNA and chromosomal DNA is removed in the first step and 90% of the nucleic acid in the eluted peak is plasmid. In the second polishing step only 0.6% of chromosomal DNA was found. The plasmid prepared by this methodology has the purity which is required for gene therapy or pharmaceutical applications.

The first chromatography step was scaled up, using Q Sepharose XL in a 100 ml column (Table 1). The results were comparable to those obtained in small scale.

The two chromatographic steps can be performed within three hours after the clear lysate has been prepared. The whole process including fermentation, harvesting of cells, cell lysis addition of calcium chloride, centrifugation filtration and chromatography can be performed within a day, thus making the present process a very efficient and speady process suitable for large scale production.

What is claimed is:

1. A process for purification of plasmid DNA by separation on an insoluble matrix comprising the following steps:
    a) lysing cells containing said plasmid DNA to obtain a lysate comprising plasmid DNA, chromosomal DNA and RNA;
    b) precipitating most of the RNA and most of the chromosomal DNA in the lysate by adding divalent alkaline earth metal ions to the lysate from step a);
    c) removing the precipitated RNA and chromosomal DNA from the lysate from step b);
    d) contacting the lysate from step c) with an anion exchange matrix containing anion exchange groups to obtain purified plasmid DNA; and
    e) contacting the purified plasmid DNA from step d) with an anion exchange matrix different from the anion exchange matrix of step d) to obtain purified plasmid DNA of gene therapy grade.

2. A process according to claim 1, wherein $CaCl_2$ is added in step b) to provide the divalent alkaline earth metal ions.

3. A process according to claim 1, wherein the cells are lysed by alkaline lysis.

4. A process according to claim 1, wherein the anion exchange groups of the matrix in step d) are bound to the matrix via extenders.

5. A process according to claim 4, wherein the matrix is a cross-linked agarose matrix and the extenders are dextran.

6. A process according to claim 1, wherein the anion groups in step d) are quaternary ammonium groups.

7. A process according to claim 1, wherein the anion exchange matrix in the step d) is contacted with an acidic equilibrium buffer before the lysate is contacted with the matrix.

8. A process according to claim 1, wherein after contact of the lysate with the anion exchange matrix in step d), said anion exchange matrix is contacted with elution buffers in two steps using a first elution buffer and a second elution buffer, the first elution buffer having a higher ion strength than the second and both being alkaline.

9. A process according to claim 8, wherein; after the anion exchange matrix is contacted with said first and second elution butters, a buffer with increased ionic strength and a high pH is contacted with the anion exchange matrix to complete the elution of RNA and subsequently elute the plasmid DNA at a slow speed.

10. A process according to claim 1, wherein the anion exchange matrix in step e) is a hydrophilyzed polystyrene/divinyl benzene matrix substituted with quaternary ammonium groups.

* * * * *